United States Patent

Waag et al.

[11] Patent Number: 6,003,377
[45] Date of Patent: Dec. 21, 1999

[54] METHOD FOR MEASURING THE THICKNESS OF PLATE CONSTRUCTIONS AND PIPE

[75] Inventors: Tor Inge Waag, Trondheim; Anette Olsen, Oslo, both of Norway

[73] Assignee: Red Band AS, Oslo, Norway

[21] Appl. No.: 08/921,761

[22] Filed: Aug. 26, 1997

Related U.S. Application Data

[63] Continuation of application No. 08/530,347, filed as application No. PCT/NO94/00060, Mar. 17, 1994, abandoned.

[30] Foreign Application Priority Data

Apr. 2, 1993 [NO] Norway ...................................... 931295

[51] Int. Cl.⁶ .................................................. G01N 29/26
[52] U.S. Cl. ................................ 73/625; 702/171; 73/628
[58] Field of Search ............................. 367/907; 702/35, 702/170, 171; 73/618, 620, 622, 625, 627, 602, 628

[56] References Cited

U.S. PATENT DOCUMENTS

| | | | |
|---|---|---|---|
| 4,212,258 | 7/1980 | Collins | 114/312 |
| 4,441,369 | 4/1984 | Lessard et al. | 73/602 |
| 4,596,144 | 6/1986 | Panton et al. | 73/620 |
| Re. 4,596,144 | 10/1995 | Panton et al. | 73/620 |
| 4,799,177 | 1/1989 | Sarr | 364/563 |
| 5,047,990 | 9/1991 | Gafos et al. | 367/6 |

FOREIGN PATENT DOCUMENTS

| | | |
|---|---|---|
| 0 139 867 | 5/1985 | European Pat. Off. . |
| 0 352 117 | 1/1990 | European Pat. Off. . |
| 2 076 154 | 11/1981 | United Kingdom . |
| 94 23311 | 10/1994 | WIPO . |

Primary Examiner—Christine K. Oda
Attorney, Agent, or Firm—Nawrocki, Rooney & Sivertson, P.A.

[57] ABSTRACT

A method for automatic state control, inspection, cleaning and/or surface treatment of structures, especially measuring the thickness of plate constructions and pipes by means of ultrasound signals from a self-propelled, remotely controllable unit. The self-propelled unit is continuously moved in the measurement area, and a transmitter transmits an ultrasound signal in a direction substantially perpendicular to the surface of the construction. A reflected signal is received by a receiver which determines thickness and material quality of the construction at the measurement spot, on the basis of the received reflected signal, and parameters such as transit time for the reflected signal. The self-propelled unit performs self-positioning by means of previously known spots on the construction. All received data regarding the waveform of the reflected signal is stored in a computer, and thickness and material quality are verified by comparing data for a received signal in one spot, with data for received signals in adjacent spots. The steps are repeated for collection of data in new measurement spots.

10 Claims, 6 Drawing Sheets

METHOD FOR MEASURING THE THICKNESS OF PLATE CONSTRUCTIONS AND PIPE

This is a continuation of application Ser. No. 08/530,347 filed on Jan. 16, 1996, now abandoned which is a 371 of PCT/NO94/00060 filed Mar. 17, 1994.

BACKGROUND OF THE INVENTION

1. Field of the Invention

The present invention concerns a method for automatic state control, inspection, cleaning and/or surface treatment of structures, especially measuring the thickness of plate constructions and pipes by transmitting ultrasound signals from at least one transmitter and receiving the ultrasound signals from at least one receiver, where the transmitter and receiver are mounted to a self-propelled, remote controlled unit, and where a liquid membrane is present between the transmitter and the surface of the structure.

2. Description of the Prior Art

When, for example, a ship is to be classified, it is necessary to collect information concerning the remaining thickness of the plates in order to calculate the strength of the hull and to certify the ship for continued operation. Furthermore, for the shipowners it is desirable to obtain knowledge of the condition and the progress of the ship in order to perform overhauling and preventive maintenance in the most efficient way, optionally to make a strategic decision of taking the ship out of operation and sell it as scrap iron, at the correct point in time.

Today, the thickness of marine steel constructions such as ships and drilling plateforms are measured by manual spot measurements (sampling test according to a certain system) which are conducted from the interior or from the exterior by a diver with a hand held measuring apparatus when the ship is in harbor. Interior measurements may also be performed in empty tanks during transit.

The prior method has obvious disadvantages. Full coverage of the hull of the ship is not achieved, and selection of the position of the measurement spot is a subjective judgment. The strength of the reflected ultrasound signal is highly dependent upon the condition of the rear wall, and in areas having corrosion pitting (a common and dangerous phenomenon), the distance between areas having full remaining thickness and areas corroded close to the danger point will be small. Between these adjacent extremes of thickness, the rear wall will necessarily slant. The transmitted signal will thus mainly be reflected to the side of the receiver which only receives a weak signal. The inspector is taught to reject weak measurements in accordance with certain criteria. By moving the measuring probe a few centimeters, the inspector will register a strong signal from an almost flat rear wall with full plate thickness. The ship may then pass the control, and the shipowner has got poor basis for decisions concerning preventive maintenance on the ship. At a later docking, the actual situation will become clear, and the subsequent remedial work will be alot more expensive than planned.

From EP 0 139 867, is known a self-propelled unit having transmitters and receivers for ultrasound signals for determining the material quality of a body. This known system is not suited for elimination of single measurements with weak signals.

SUMMARY OF THE INVENTION

It is therefore an object of the present invention to provide a method of the above-mentioned kind, which may be utilized for different tasks on structures in liquid and structures filled with liquid.

The object of the invention is achieved with a method for automatic state control, inspection, cleaning and/or surface treatment of structures, especially measuring the thickness of plate constructions and pipes, by transmitting ultrasound signals from at least one transmitter and receiving the ultrasound signals from at least one receiver, where the transmitter and receiver are mounted to a self-propelled, remote controlled unit, and where a liquid membrane is present between the transmitter and the surface of the structure.

BRIEF DESCRIPTION OF THE DRAWINGS

In the following, an embodiment of the invention will be explained by way of example and with reference to the accompanying drawings, in which.

DETAILED DESCRIPTION OF THE PREFERRED EMBODIMENTS

In the example, the invention is explained in connection with ultrasound measurement of a ship's hull. However, it should be appreciated that the invention can also be adapted for use in connection with other marine steel constructions, or constructions in other materials.

Figure 1:
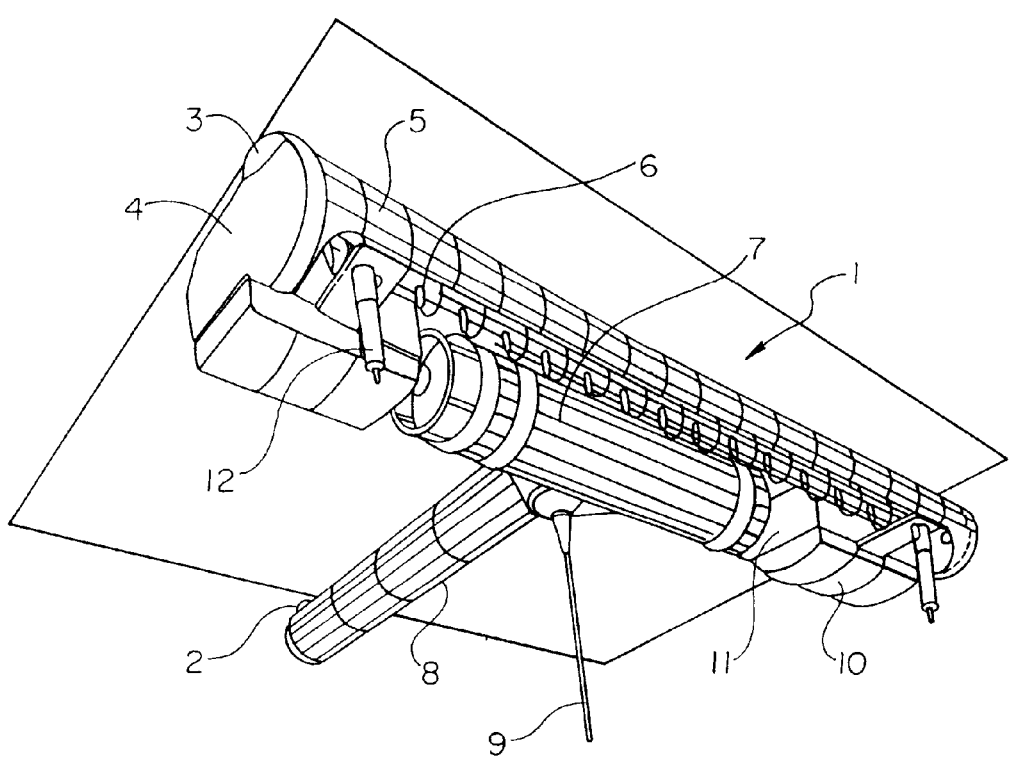
FIG. 1 shows an example of a device for carrying out the invention.

Referring firstly to FIG. 1, there is shown a self-propelled unit 1 having three wheels 2 and 3 mounted to a frame 4. To the frame 4 is also mounted a measuring beam 5 and a steering arm 8, which steering arm extends from and transverse to the middle section of the measuring beam. The unit 1 is operated by at least one motor (not shown). The two wheels 3 are situated one at each end of the measuring beam 5 and the wheel 2 is situated at the free end of the steering arm 8. Thus, in use, the measuring beam extends perpendicular to the direction of movement of the unit 1, and the steering arm 8 extends along the direction of movement.

A number of ultrasound probes 6 are mounted to the measuring beam 5. In a preferred embodiment, 16 such probes 6 are used. The probes 6 are connected to a computer 7 located in a cylinder situated parallel to the measuring beam 5. From the computer 7, a cable extends to a further computer on-board the ship.

At each end outside the computer 7 are located buoyancy cushions 10 situated in boxes 11. The buoyancy of the cushions 10 may be regulated by an air supply from an air tank (not shown), and outlet from an override pressure relief valve. The equipment initially has a neutral buoyancy in water.

Situated at the ends of the measuring beam are two positioning lights 12, which are utilized in positioning the unit 1.

In use, the unit 1 is situated under a ship hull by a diver. The diver also has site positioning lights under the ship, for example, one light in three corners of a rectangular operation area. The unit 1 is located in a known initial spot. By means of the computer 7, the unit, oriented by means of the positioning lights, is guided back and forth along the bottom of the ship.

Each of the probes 6 transmits signals against the plate being measured. The signal is transmitted as a pulse, and the reflected signal is registered and stored. Transmitter and receiver may be one and the same unit, which is electronically switched from transmission to reception. The total wave for the reflected signal is stored, not only transit time for the different parts of the signal. This renders possible any post-processing for quality control. This demands that a computer is available in the vicinity of the probes.

Figure 2:
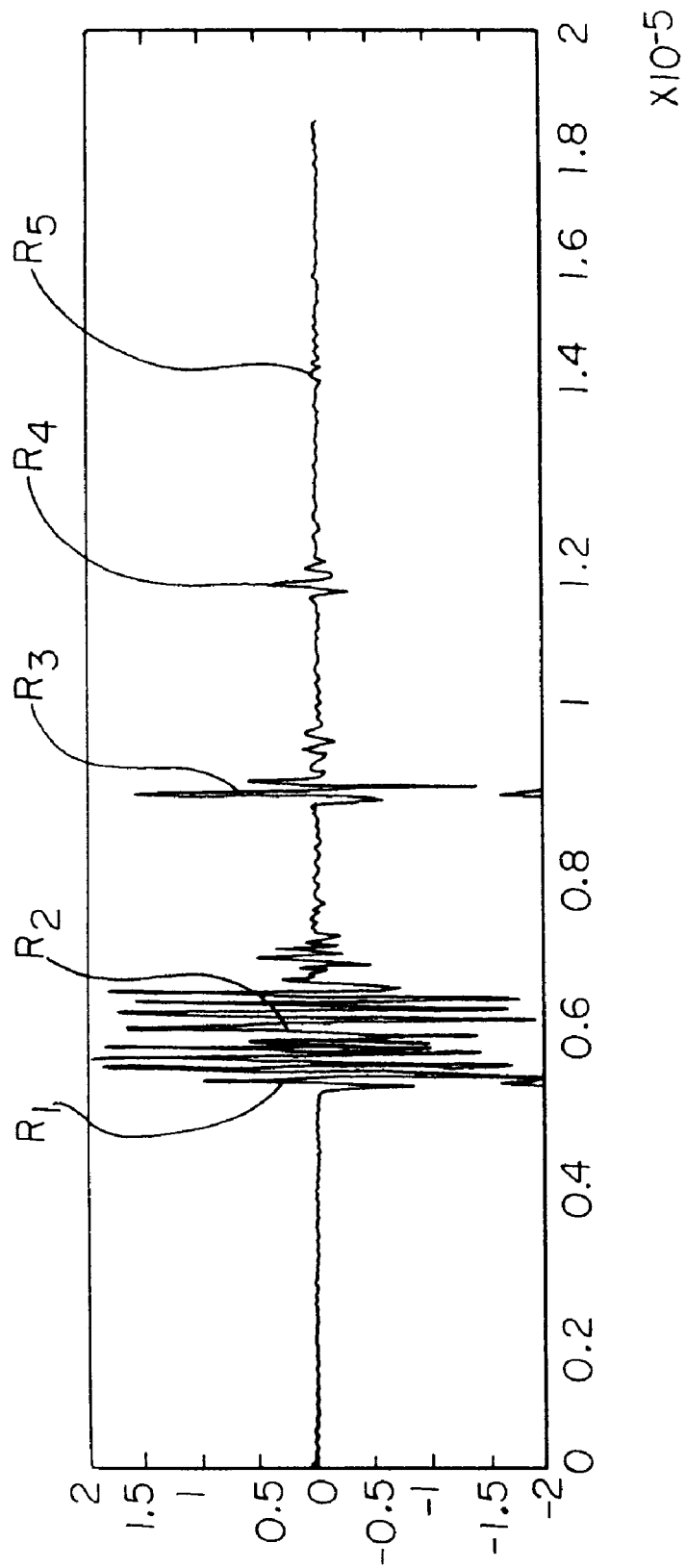
FIG. 2 shows a graphic representation of a received reflected signal in one measurement spot, wherein the x-axis denotes the time for transmitted signal and the y-axis denotes the strength of the signal.

FIG. 2 shows a received reflected signal. In the graphic presentation, the y-axis denotes the signal strength, which is a representation of the degree of reflection. The x-axis denotes the progress of the reflected signal on a time basis. Considering the velocity of the ultrasound signal, the time axis will represent a measure of the thickness at the measuring spots.

The area in FIG. 2 which is marked $R_1$ is descended from the measuring on the outside of the steel plate. This area contains components which have travelled back and forth several times in the paint layer. The area $R_2$ shows the reflected signal from the outside of the steel plate, whereas $R_3$ shows the signal being reflected from the rear wall of the plate. $R_4$ and $R_5$ respectively show second and third order reflections from the rear wall. It should also be noted that it is a constant interval between $R_2$, $R_3$, $R_4$, and $R_5$.

The signal progress shown in FIG. 2 is typical for a reflected signal from a measured steel plate of a certain dimension. In many cases, the reflected signal may be weaker. This applies, for example, when a weaker section of a plate has a slanted surface. The main part of the reflected signal will then be directed away from the probe transmitting the signal. Some of the reflected signal will be received by the probe 6, but it will be a weak signal. By manual measurement, such signals will be rejected. According to the present invention, the reflected signal will be processed, or treated on the basis of stored raw data. This is achieved by two and three dimensional filtering.

Two dimensional filtering is a method known from processing of seismic data. It aims at adapting conventional filtering techniques (smoothing, removal of noise or unwanted frequency components, increasing wanted frequency components) usually being utilized for one dimensional time series of data, for a collection of such one dimensional time series of data, for example, samples in adjacent spots along a line. The data set is then called two dimensional, as the time axis is the first dimension and the location axis is the other dimension.

By expansion to three dimensions, data is collected in a grid system in a plane, so that data is collected from all the spots in the plane in separate time series. Two and three dimensional filtering can be used, for example, for smoothing and removal of noise or to increase certain trends in the data set along the first or the second axis (location or time), or in a diagonal direction in the reference frame. Frequency analysis may be conducted along a free number of axes in this system in order to emphasize certain characteristic properties in the data set.

Figure 4:
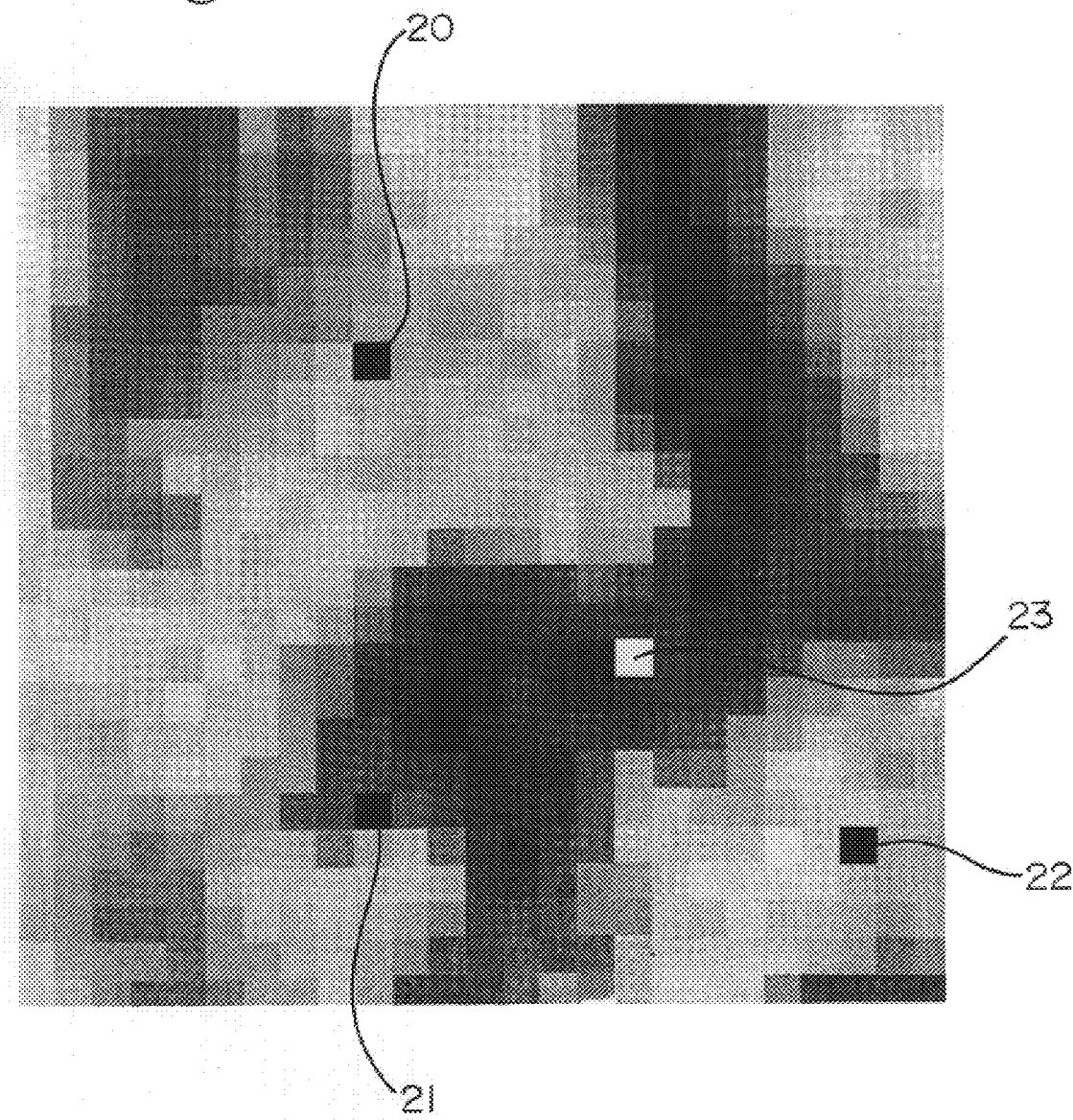
FIG. 4 shows the plate part in FIG. 3, measured according to the present invention, and displayed in a gray scale.

FIG. 4 shows a presentation of the plate part of FIG. 2, after being measured according to the present invention. The result is presented in a gray scale, where lighter shade means thicker plate. In FIG. 4, the spots 20, 21, 22, and 23 are marked. It may be seen that spots 20–22 are completely black, indicating very thin sections. Furthermore, spot 23 is completely white, indicating a very thick section. However, it may be seen for all these spots that it is not an even transition from one spot to the next. It is therefore reasonable to believe that these are erroneous measurements. These will be eliminated by three dimensional filtering according to the present invention.

Figure 3:
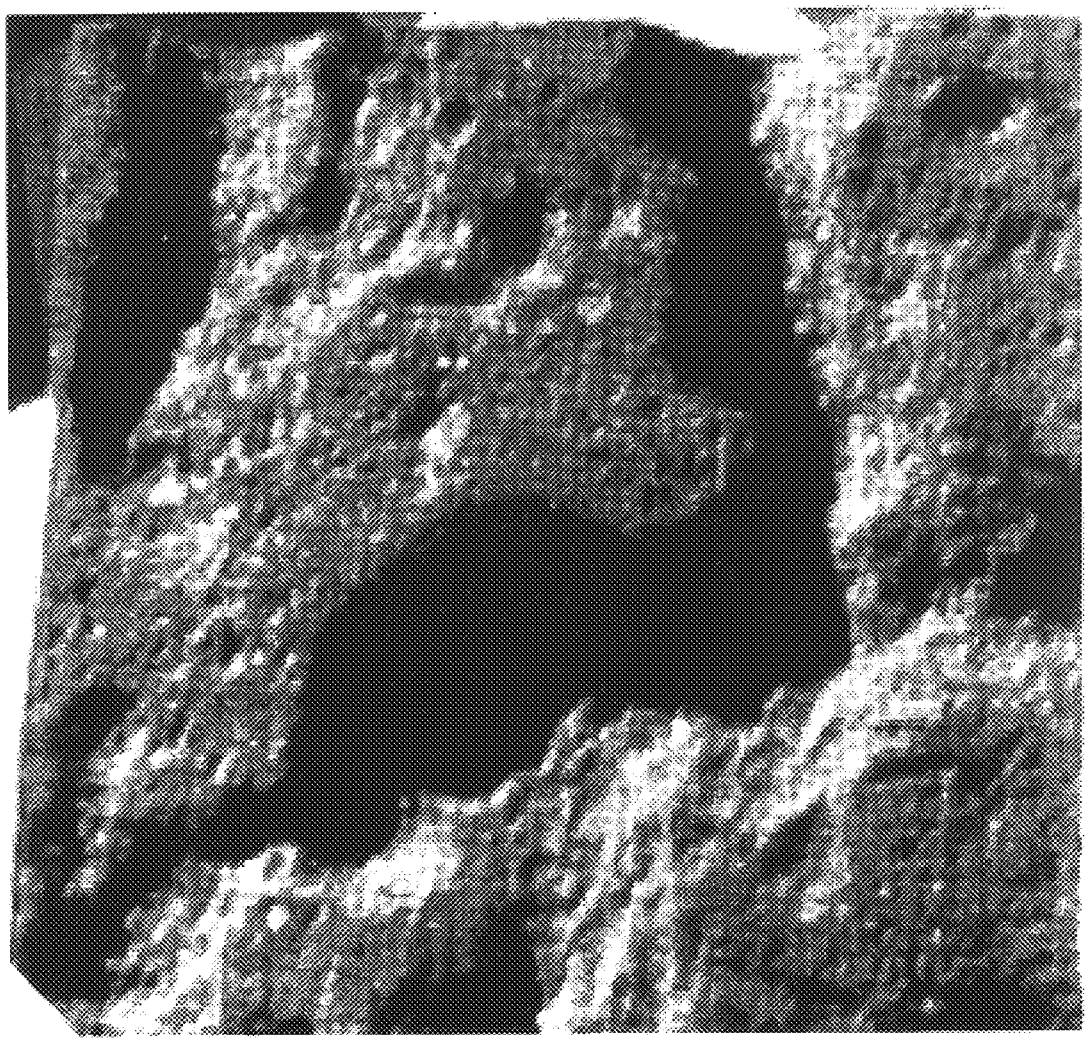
FIG. 3 shows a plate part having different thickness due to corrosion pitting.
Figure 5:
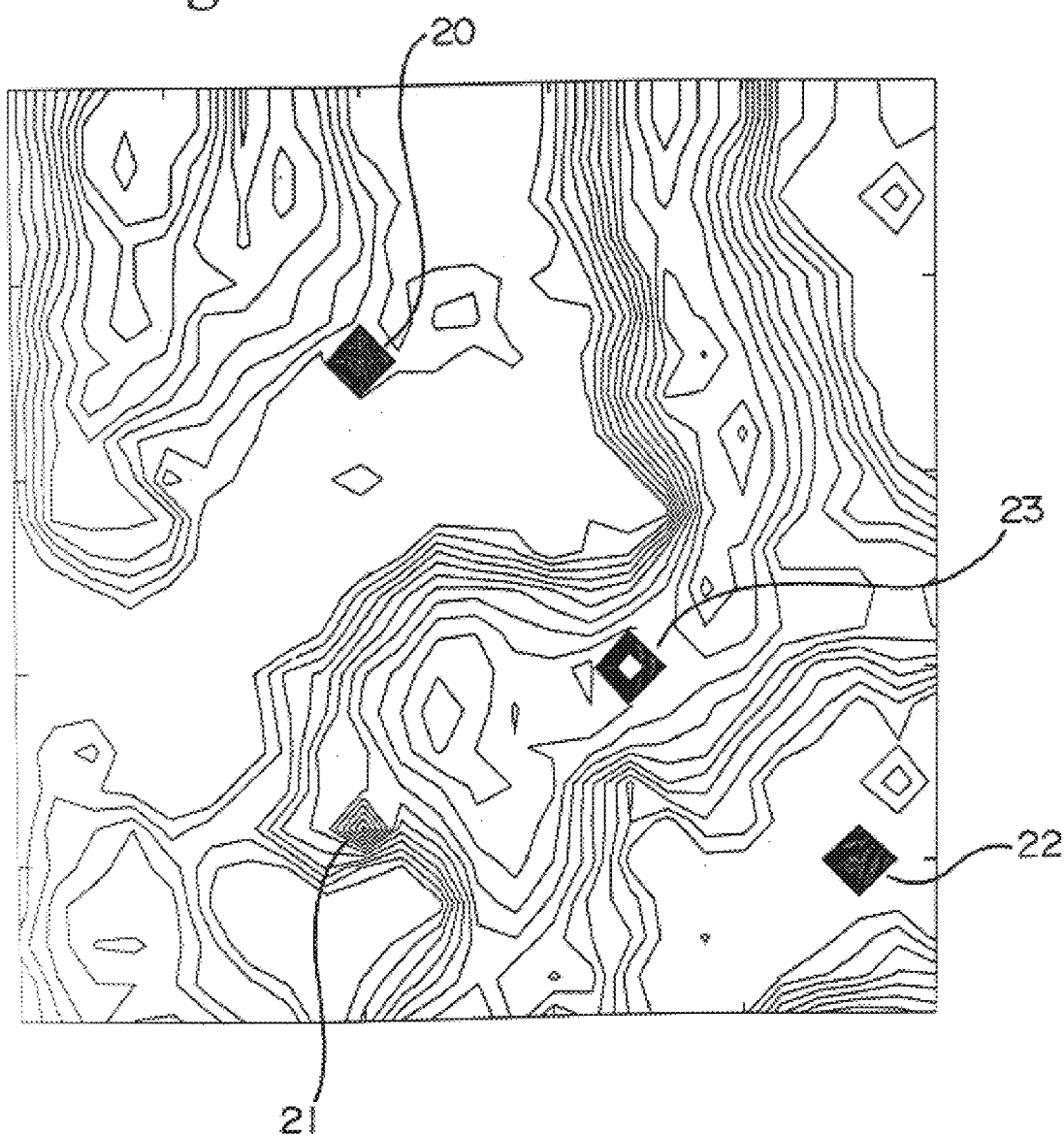
FIG. 5 shows the plate part in FIG. 3, measured according to the present invention, and displayed as a contour map.
Figure 6:
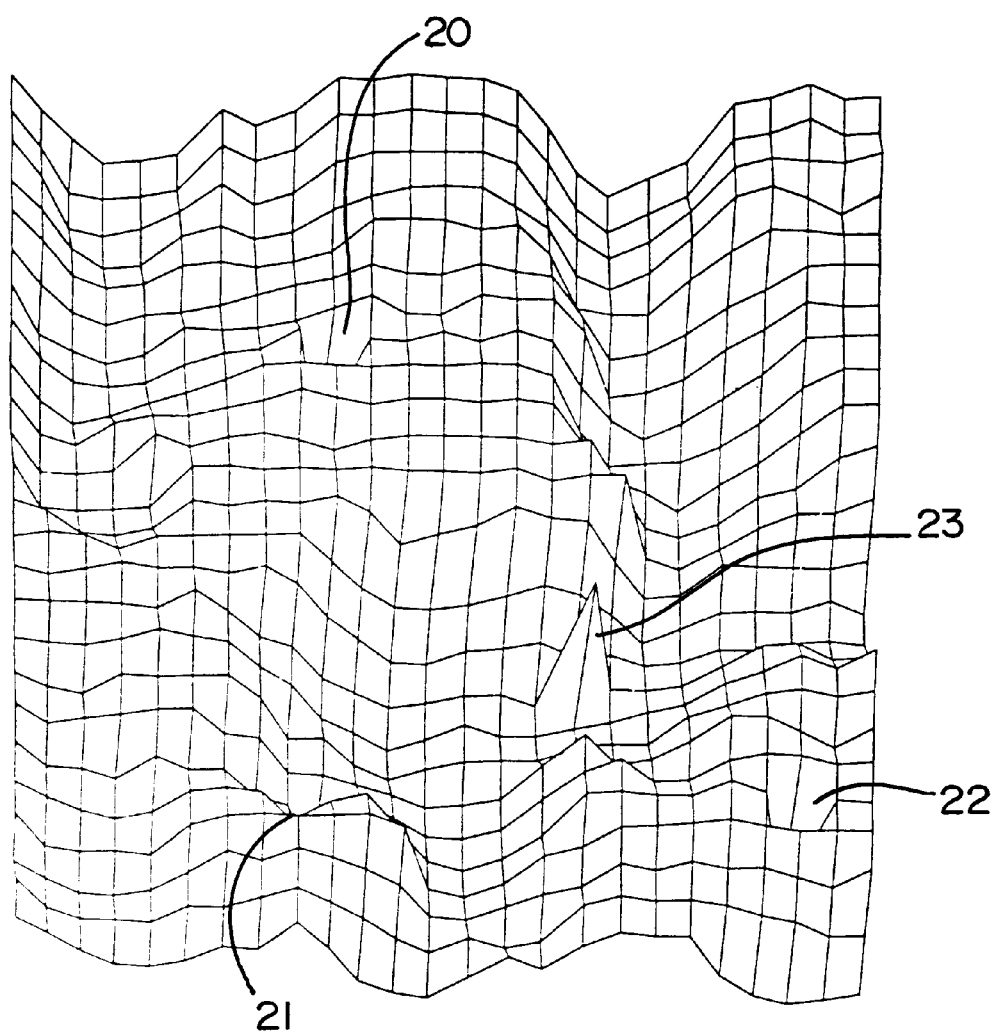
FIG. 6 shows the plate part in FIG. 3, measured according to the present invention, and displayed as a topographic terrain model.

The same spots 20–23 can be found in FIGS. 5 and 6, which are representations as a contour map and a terrain model, respectively. If the terrain mode in FIG. 6 is compared with the photo in FIG. 3, it can be seen that the spots probably are erroneous measurements.

The unit 1 has comparatively small dimensions, a preferred embodiment has a width of a little more than one and a half meters. This implies that the equipment can be easily transported and may, for example, be transported by an airplane. By using a device according to the present invention, the total ship may be covered with a sufficient degree of accuracy to map corrosion pitting during a period corresponding to a normal load/unload time (24 hours).

The unit may be operated independently of a diver by using thrusters for propulsion. The unit 1 is also devised to be able to carry other inspecting systems, such as video inspection, or conduct other relevant tasks below the ship, such as cleaning. If the equipment is to be used on the side of the ship, attachment/propulsion may be achieved by means of magnets.

The equipment can also be operated above the surface. In order to achieve sufficient transmission of the ultrasound signal, it is preferred to flush with water between the ship's side and the probes.

In an initial examination of a ship, a map of the ship may be produced, and structural elements such as ribs, struttings and plate joints can be drawn in where detected. This map may be later used for self-positioning the unit 1 by means of the illustrated structural elements. During later measurements, a map of the thickness of the ship can be compared with the constructional drawings, so that certain plates or hull components can be identified for replacement.

According to the present invention, full ultrasound waveforms are stored (not only the transit time) for any required post-processing. The system has sufficient solution in thickness and sufficient accuracy in positioning for subtraction of measurements taken at different points in time provides the time progress of corrosion. By means of a high-capacity data cable to the surface, a computer on the deck can operate in tandem with the submerged computer, so that a large amount of data can be stored on replaceable media (replaceable discs, disc tape, optical discs, etc.). The stored set of data is sufficient to be included in strength calculations of the ship.

The rate of coverage, or the distance of the spot measurements, can be automatically varied by the unit on the basis of the statistic properties of the data. Thus, the inspection may take place faster over homogenous areas of good quality, whereas areas with larger deviations in thickness or signal strength should be examined closer. However, it is a substantial point that sufficient data is collected, so that it is not necessary to return to conduct further examinations.

The device may also be used upon other materials, such as plastics, glass fiber reinforced plastics, aluminum, etc. The device may also be used for inspection in pipes, tanks, and so on.

We claim:

1. Method for automatic state control, inspection, cleaning and/or surface treatment of a structure, including measuring the thickness of plate constructions and pipes by transmitting ultrasound signals from at least one transmitter, being received by at least one receiver, said at least one transmitter and said at least one receiver being mounted to a self-propelled, remotely controllable unit, a liquid membrane being present between the at least one transmitter and the surface of the structure; the method comprising:

continuously moving the self-propelled unit on the surface of the structure in a controlled fashion, transmitting ultrasound signals from the at least one transmitter in a direction substantially perpendicular to a plate being measured, receiving a reflected signal by the receiver, and determining thickness and material quality of the plate at a measuring spot, on the basis of the reflected signal, and transit time for the reflected signal and material constants for subsequent measurement spots, characterized by the self-propelled unit being self-positioning by means of previously known spots on the plate, all received data regarding waveform of the reflected signal is stored in a computer, thickness and material quality being verified by comparing data for the received signal in one spot, with data for received signals in adjacent spots.

2. Method according to claim 1, characterized by the comparison of data between adjacent spots being performed by two-dimensional filtering.

3. Method according to claim 1, characterized by the comparison of data between adjacent spots being performed by three-dimensional filtering.

4. Method according to claim 1, characterized by the stored data being processed in order to provide a topographical map showing both thickness and known structural elements of the plate.

5. Method according to claim 1, characterized by the self-propelled unit initially being positioned on the plate by means of a high precision hydro-acoustic positioning system, and/or by means of known reference spots upon the plate.

6. Method according to claim 1, characterized by the self-propelled unit being moved along a surface of the plate according to a predetermined line pattern, and through automatic steering.

7. Method according to claim 1, characterized by the positioning of the self-propelled unit initially being performed by means of a high precision hydro-acoustic positioning system and position references established in advance.

8. Method according to claim 1, characterized by initial positioning of the self-propelled unit performed autonomously, without position references being established in advance, by comparing the collected data with construction drawings for the structure, and/or data from previous inspections.

9. Method according to claim 1, characterized by the collection of measurement data being varied autonomously on the basis of the statistic properties of the collected data, whereas the examination is performed faster upon homogenous areas of good quality, while areas having a larger spread in thickness or signal strength are subject to closer examination.

10. Method according to claim 1, characterized by the data from the computer being transferred to a second computer, through a high capacity transmission line, in order to provide for storage of large amounts of data, real-time processing, presentation and quality control of the collected measurement data.

* * * * *